United States Patent
Finley et al.

(10) Patent No.: US 12,201,381 B2
(45) Date of Patent: *Jan. 21, 2025

(54) SYSTEMS AND METHODS FOR SPINAL SURGICAL PROCEDURES

(71) Applicant: NuVasive, Inc., San Diego, CA (US)

(72) Inventors: Eric Finley, San Diego, CA (US); Justin Smith, San Diego, CA (US)

(73) Assignee: Globus Medical Inc., Audubon, PA (US)

( * ) Notice: Subject to any disclaimer, the term of this patent is extended or adjusted under 35 U.S.C. 154(b) by 298 days.

This patent is subject to a terminal disclaimer.

(21) Appl. No.: 17/843,645

(22) Filed: Jun. 17, 2022

(65) Prior Publication Data

US 2022/0313366 A1    Oct. 6, 2022

Related U.S. Application Data

(63) Continuation of application No. 16/562,411, filed on Sep. 5, 2019, now Pat. No. 11,399,897.

(Continued)

(51) Int. Cl.
*A61B 34/30* (2016.01)
*A61B 34/00* (2016.01)
(Continued)

(52) U.S. Cl.
CPC .............. *A61B 34/20* (2016.02); *A61B 34/25* (2016.02); *A61B 34/30* (2016.02);
(Continued)

(58) Field of Classification Search
CPC ......... A61B 34/00; A61B 34/10; A61B 34/20; A61B 34/30; A61B 34/25;
(Continued)

(56) References Cited

U.S. PATENT DOCUMENTS

| | | | |
|---|---|---|---|
| 6,522,906 B1 * | 2/2003 | Salisbury, Jr. | A61B 1/0005 600/407 |
| 9,789,608 B2 | 10/2017 | Itkowitz et al. | |
| 9,867,721 B2 | 1/2018 | Hunter | |
| 11,065,065 B2 * | 7/2021 | Rezach | A61B 34/20 |
| 11,399,897 B2 * | 8/2022 | Finley | A61B 34/30 |
| 2008/0065109 A1 * | 3/2008 | Larkin | A61B 1/00154 901/14 |

FOREIGN PATENT DOCUMENTS

| | | |
|---|---|---|
| JP | 2001-104333 | 4/2001 |
| JP | 2007-29232 | 8/2008 |

(Continued)

OTHER PUBLICATIONS

Japanese Refusal in Application 2021-512572, mailed Jun. 23, 2022, 9 pages.

(Continued)

*Primary Examiner* — Vi X Nguyen (57) ABSTRACT

A method comprising capturing a pose of a surgical tool at a surgical site of a patient. The method includes determining a range of movement of the surgical tool at the surgical site, in response to the captured pose. The method includes displaying a representation of the determined range of movement onto an image associated with the surgical site. The method includes providing one or more instructions to limit a movement of a robotic device according to the determined range of movement.

16 Claims, 7 Drawing Sheets

Related U.S. Application Data (60) Provisional application No. 62/727,537, filed on Sep. 5, 2018.

(51) Int. Cl.
  *A61B 34/20* (2016.01)
  *A61B 34/10* (2016.01)

(52) U.S. Cl.
  CPC .................. *A61B 2034/107* (2016.02); *A61B 2034/2055* (2016.02); *A61B 2034/303* (2016.02)

(58) Field of Classification Search
  CPC ...... A61B 2034/107; A61B 2034/2055; A61B 2034/303; A61B 19/203; A61B 19/5244
  See application file for complete search history.

(56) References Cited

FOREIGN PATENT DOCUMENTS

| | | |
|---|---|---|
| JP | 2012-521855 | 9/2012 |
| JP | 2017-515524 | 6/2017 |
| WO | 2014/104088 | 7/2014 |
| WO | 2015142512 | 9/2015 |

OTHER PUBLICATIONS

PCT International Preliminary Report on Patentability in Application PCT/US2019/049826, mailed Mar. 18, 2021, 9 pages.
PCT International Search Report; ISA/EP; PCT/US2019/049826; dated Dec. 16, 2019, 5 pgs.
PCT Written Opinion of the International Search Authority, ISA/EP, PCT/US2019/049826, dated Dec. 16, 2019, 7 pgs.

* cited by examiner

SYSTEMS AND METHODS FOR SPINAL SURGICAL PROCEDURES

CROSS-REFERENCE TO RELATED APPLICATION

This application is a continuation of U.S. patent application Ser. No. 16/562,411, filed on Sep. 5, 2019, which claims the benefit of and priority to U.S. Provisional Application No. 62/727,537, filed on Sep. 5, 2018, the entire disclosures of which are incorporated herein by reference.

FIELD

This disclosure describes motion programming of a robotic device based on a tracked surgical instrument.

BACKGROUND

Minimally invasive surgery typically limits the size of incisions into a human body so that the recovery from surgical procedures may be quick and the odds of infection reduced. However, only a few tools may be concurrently used by the same surgeon during minimally invasive surgery. Sometimes a tool change may occur to place the proper tool with the surgical suite. A tool change may extend out of time of a minimally invasive surgical procedure. Moreover, minimally invasive surgery may be burdensome on a surgeon, particularly when manually operating surgical controls for long periods of time.

SUMMARY

In one embodiment, a method comprises capturing a pose of a surgical tool at a surgical site of a patient. The method also comprises determining a range of movement of the surgical tool at the surgical site, in response to the captured pose. The method also comprises displaying a representation of the determined range of movement onto an image associated with the surgical site. The method also comprises providing one or more instructions to limit a movement of a robotic device according to the determined range of movement.

In another embodiment, a system comprises a tracking device, a robotic device, and a processing device. The processing device comprises a processor and a non-transitory computer readable medium having stored thereon instructions that, when executed by the processor, cause the system to capture, via the tracking device, a pose of a surgical tool at a surgical site of a patient. The stored thereon instructions that, when executed by the processor, also cause the system to determine, by the processor, a range of movement of the surgical tool at the surgical site, in response to the captured pose. The stored thereon instructions that, when executed by the processor, also cause the system to display a representation of the determined range of movement onto an image associated with the surgical site. The stored thereon instructions that, when executed by the processor, also cause the system to provide one or more instructions to limit a movement of a robotic device according to the determined range of movement.

In another embodiment, a method comprises capturing a pose of a surgical tool at a surgical site of a patient, wherein the surgical tool is coupled to a robotic device. The method also comprises determining an axis for pivoting the surgical tool and a range of degrees within one or more planes for pivoting the surgical tool about the axis, in response to the captured pose. The method also comprises displaying a representation of at least one of the axis and the range of degrees on a display. The method also comprises providing one or more instructions to limit a movement of the robotic device according to the axis and the range of degrees within the one or more planes.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to active the developers' specific goals, such as compliance with system-related and business-related constraints, which will vary from one implementation to another. Moreover, it will be appreciated that such a development effort might be complex and time-consuming, but nevertheless be a routine undertaking for those of ordinary skill in the art having the benefit of this disclosure. It is furthermore to be readily understood that, although discussed below primarily within the context of spinal surgery, the systems and methods of the present invention may be employed in any number of anatomical settings to provide access to any number of different surgical target sites throughout the body.

Examples described herein include systems and methods for performing a surgical procedure. In one example, a method includes capturing a pose of a surgical tool at a surgical site of a patient. In one scenario, the surgical tool is coupled to a robotic device. In this scenario, a user (e.g., surgeon) may guide the surgical tool to the surgical site with assistance by the robotic device.

The method also includes, in response to the captured pose, determining a range of movement of the surgical tool at the surgical site. In one example, the determined range of movement may be based be conical according to a determined axis of the surgical tool. In another example, the determined range of movement may be determined along the edge of a surgical tool such as a retractor. In this example, the range of movement may be limited to one or more arms of the retractor.

The method also includes display a representation of the determined range of movement onto an image associated with the surgical site. In one example, the image may be a two-dimensional image or three-dimensional image of the surgical site. In another example, the image of associated with the surgical site may be a pre-operative or intra-operative image of the patient.

The method also includes providing one or more instructions to limit a movement of a robotic device according to the determined range of movement. For example, the robotic device may be configured to assist with a surgical procedure involving the use of one or more pedicle screws. In this example, a surgeon may guide a surgical tool coupled to the robotic device to one or more pedicles associated with one more vertebrae. Based on the captured pose of the surgical tool, the one or more instructions may further limit movement of the robotic device in order to avoid breaching a perimeter of the pedicle when inserting the one or more pedicle screws in the one or more vertebrae.

Figure 1:
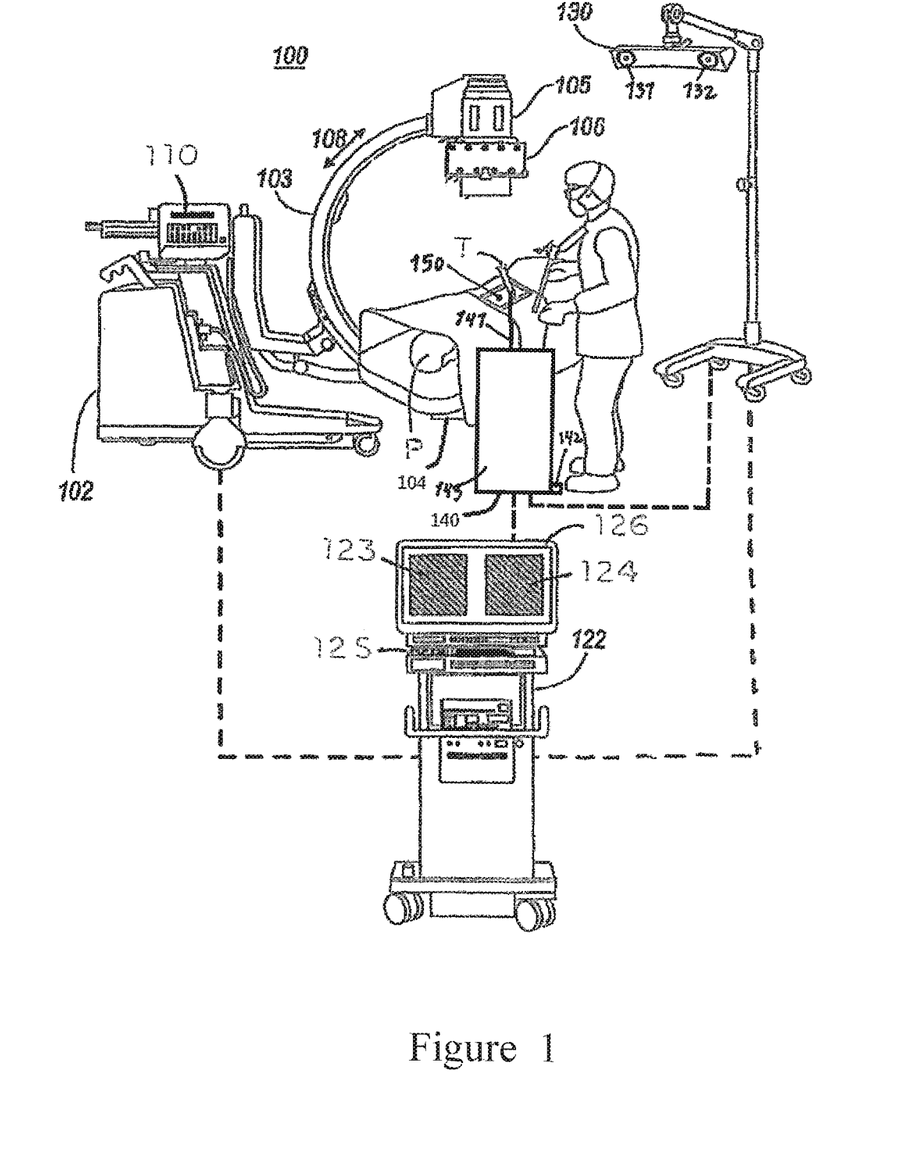
FIG. 1 illustrates an example system for performing a surgical procedure, according to an embodiment of the present disclosure.

Referring now to the figures, FIG. 1 is a diagram of an example system 100 for performing a surgical procedure. The example system 100 includes a base unit 102 supporting a C-Arm imaging device 103. The C-Arm 103 includes a radiation source 104 that is positioned beneath the patient P and that directs a radiation beam upward to the receiver 105. The receiver 105 of the C-Arm 103 transmits image data to a processing device 122. The processing device 122 may communicate with a tracking device 130 to obtain position and orientation information of various instruments (e.g., instrument T) used during the surgical procedure. The tracking device 130 may communicate with a robotic device 140 to provide location information of various tracking elements, such as marker 150. The robotic device 140 and the processing device 122 may communicate via one or more communication channels.

The base unit 102 includes a control panel 110 through which a user can control the location of the C-Arm 103, as well as the radiation exposure. The control panel 110 thus permits the radiology technician to "shoot a picture" of the surgical site at a surgeon's direction, control the radiation dose, and initiate a radiation pulse image.

The C-Arm 103 may be rotated about the patient P in the direction of the arrow 108 for different viewing angles of the surgical site. In some instances, implants or instrument T may be situated at the surgical site, necessitating a change in viewing angle for an unobstructed view of the site. Thus, the position of the receiver relative to the patient P, and more particularly relative to the surgical site of interest, may change during a procedure as needed by the surgeon or radiologist. Consequently, the receiver 105 may include a tracking target 106 mounted thereto that allows tracking of the position of the C-Arm 103 using the tracking device 130. By way of example only, the tracking target 106 may include a plurality of infrared (IR) reflectors or emitters spaced around the target, while the tracking device 130 is configured to triangulate the position of the receiver 105 from the IR signals reflected or emitted by the tracking target 106.

The processing device 122 can include a digital memory associated therewith and a processor for executing digital and software instructions. The processing device 122 may also incorporate a frame grabber that uses frame grabber technology to create a digital image for projection as displays 123 and 124 on a display device 126. The displays 123 and 124 are positioned for interactive viewing by the surgeon during the procedure. The two displays 123 and 124 may be used to show images from two views, such as lateral and A/P, or may show a baseline scan and a current scan of the surgical site, or a current scan and a "merged" scan based on a prior baseline scan and a low radiation current scan. An input device 125, such as a keyboard or a touch screen, can allow the surgeon to select and manipulate the on-screen images. It is understood that the input device may incorporate an array of keys or touch screen icons corresponding to the various tasks and features implemented by the processing device 122. The processing device 122 includes a processor that converts the image data obtained from the receiver 105 into a digital format. In some cases, the C-Arm 103 may be operating in the cinematic exposure mode and generating many images each second. In these cases, multiple images can be averaged together over a short time period into a single image to reduce motion artifacts and noise.

The tracking device 130 includes sensors 131 and 132 for determining location data associated with a variety of elements (e.g., an infrared reflector or emitter) used in a surgical procedure. In one example, the sensors 131 and 132 may be a charge-coupled device (CCD) image sensor. In another example, the sensors 131 and 132 may be a complementary metal-oxide-semiconductor (CMOS) image sensor. It is also envisioned that a different number of other image sensors may be used to achieve the functionality described.

In one aspect, the robotic device 140 may assist with holding an instrument T relative to the patient P during a surgical procedure. In one scenario, the robotic device 140 may be configured to maintain the instrument T in a relative position to the patient P as the patient P moves (e.g., due to breathing) or is moved (e.g., due to manipulation of the patient's body) during the surgical procedure.

The robotic device 140 may include a robot arm 141, a pedal 142, and a mobile housing 143. The robotic device 140 may also be in communication with a display such as display 126. The robotic device 140 may also include a fixation device to fix the robotic device 140 to an operating table.

The robot arm 141 may be configured to receive one or more end effectors depending on the surgical procedure and the number of associated joints. In one example, the robot arm 141 may be a six joint arm. In this example, each joint includes an encoder which measures its angular value. The movement data provided by the one or more encoders, combined with the known geometry of the six joints, may allow for the determination of the position of the robot arm 141 and the position of the instrument T coupled to the robot arm 141. It also envisioned that a different number of joints may be used to achieve the functionality described herein.

The mobile housing 143 ensures easy handling of the robotic device 140 through the use of wheels or handles or both. In one embodiment, the mobile housing 143 may include immobilization pads or an equivalent device. The mobile housing 143 may also include a control unit which provides one or more commands to the robot arm 141 and allows a surgeon to manually input data through the use of an interface, such as a touch screen, a mouse, a joystick, a keyboard or similar device.

In one example, the processing device 122 is configured to capture a pose of an instrument T via the tracking device 130. The captured pose of the instrument includes a combination of position information and orientation information. In this example, the pose of the instrument T is based on a user defined placement at a surgical site of the patient P. The user defined placement is based on movement of the instrument T by a surgeon or the robotic device 140 or both. In one scenario, the instrument comprises one or more infrared reflectors or emitters. Continuing with this example, the processing device 122 is configured to determine a range of movement of the instrument T corresponding to the captured pose of the instrument T. The range of movement is associated with the actuation of one or more components (e.g., one or more links and joints) of the robotic device 140. The processing device 122 is configured to determine one or more instructions for actuating the one or more components of the robotic device 140 according to the determined range of movement. Further, the processing device 122 is configured to provide the one or more instructions to the robotic device 140.

In another example, in response to the captured pose of the instrument T, the processing device 122 is configured to determine an axis for pivoting the instrument T and a range of degrees within one or more planes for pivoting the instrument T about the determined axis. In this example, the processing device 122 is configured to provide the one or more instructions to limit a movement to robotic device 140 for pivoting the instrument T coupled to the robotic device 140. The robotic device 140, as described herein, is configured to convert the one or more instructions for enabling the instrument T to be pivoted according to the determined axis and the range of degrees within one or more planes.

Figure 2:
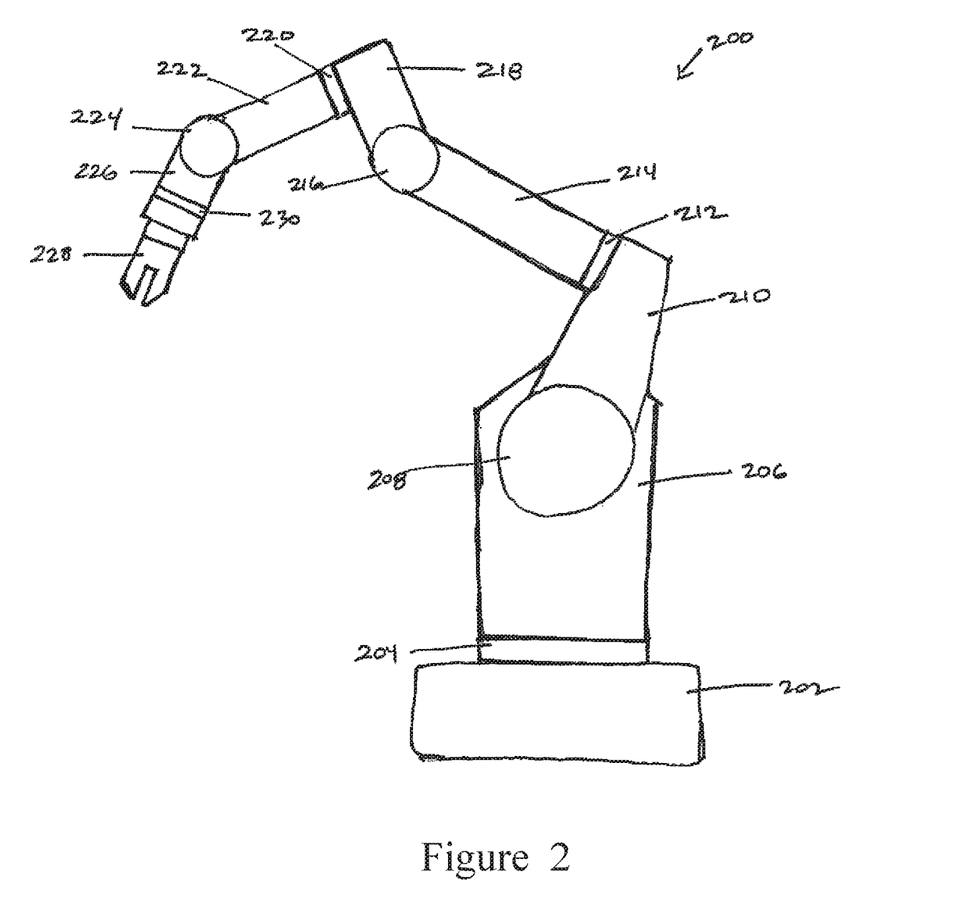
FIG. 2 illustrates an example robotic device that may be used during a surgical procedure, according to an embodiment of the present disclosure.

FIG. 2 illustrates an example robotic device 200 that may be used during a surgical procedure. The robotic device 200 may contain hardware, such as a processor, memory or storage, and sensors that enable the robotic device 200 for use in a surgical procedure. The robotic device 200 may be powered by various means such as electric motor, pneumatic motors, hydraulic motors, etc. The robotic device 200 includes a base 202, links 206, 210, 214, 218, 222, and 226, joints 204, 208, 212, 216, 220, 224, and 230, and manipulator 228.

The base 202 may provide a platform in order to provide support for the robotic device 200. The base 202 may be stationary or coupled to wheels in order to provide movement of the robotic device 200. The base 202 may comprise any number of materials such as aluminum, steel, stainless steel, etc., that may be suitable for a given environment associated with the robotic device 200.

The links 206, 210, 214, 218, 222, and 226 may be configured to be moved according to a programmable set of instructions. For instance, the links may be configured to follow a predetermined set of movements (e.g., a limited range of movements based on a captured pose of an instrument) in order to accomplish a task under the supervision of a user. By way of example, the links 206, 210, 214, 218, 222, and 226 may form a kinematic chain that defines relative movement of a given link of links 206, 210, 214, 218, 222, and 226 at a given joint of the joints 204, 208, 212, 216, 220, 224, and 230.

The joints 204, 208, 212, 216, 220, 224, and 230 may be configured to rotate through the use of a mechanical gear system. In one example, the mechanical gear system is driven by a strain wave gearing, a cycloid drive, etc. The mechanical gear system selected would depend on a number of factors related to the operation of the robotic device 200 such as the length of the given link of the links 206, 210, 214, 218, 222, and 226, speed of rotation, desired gear reduction, etc. Providing power to the joints 204, 208, 212, 216, 220, 224, and 230 will allow for the links 206, 210, 214, 218, 222, and 226 to be moved in a way that allows the manipulator 228 to interact with an environment.

In one example, the manipulator 228 is configured to allow the robotic device 200 to interact with the environment according to one or more constraints. In one example, the manipulator 228 performs appropriate placement of an element through various operations such as gripping a surgical instrument. By way of example, the manipulator 228 may be exchanged for another end effector that would provide the robotic device 200 with different functionality.

In one example, the robotic device 200 is configured to operate according to a robot operating system (e.g., an operating system designed for specific functions of the robot). A robot operating system may provide libraries and tools (e.g., hardware abstraction, device drivers, visualizers, message-passing, package management, etc.) to enable robot applications.

Figure 3:
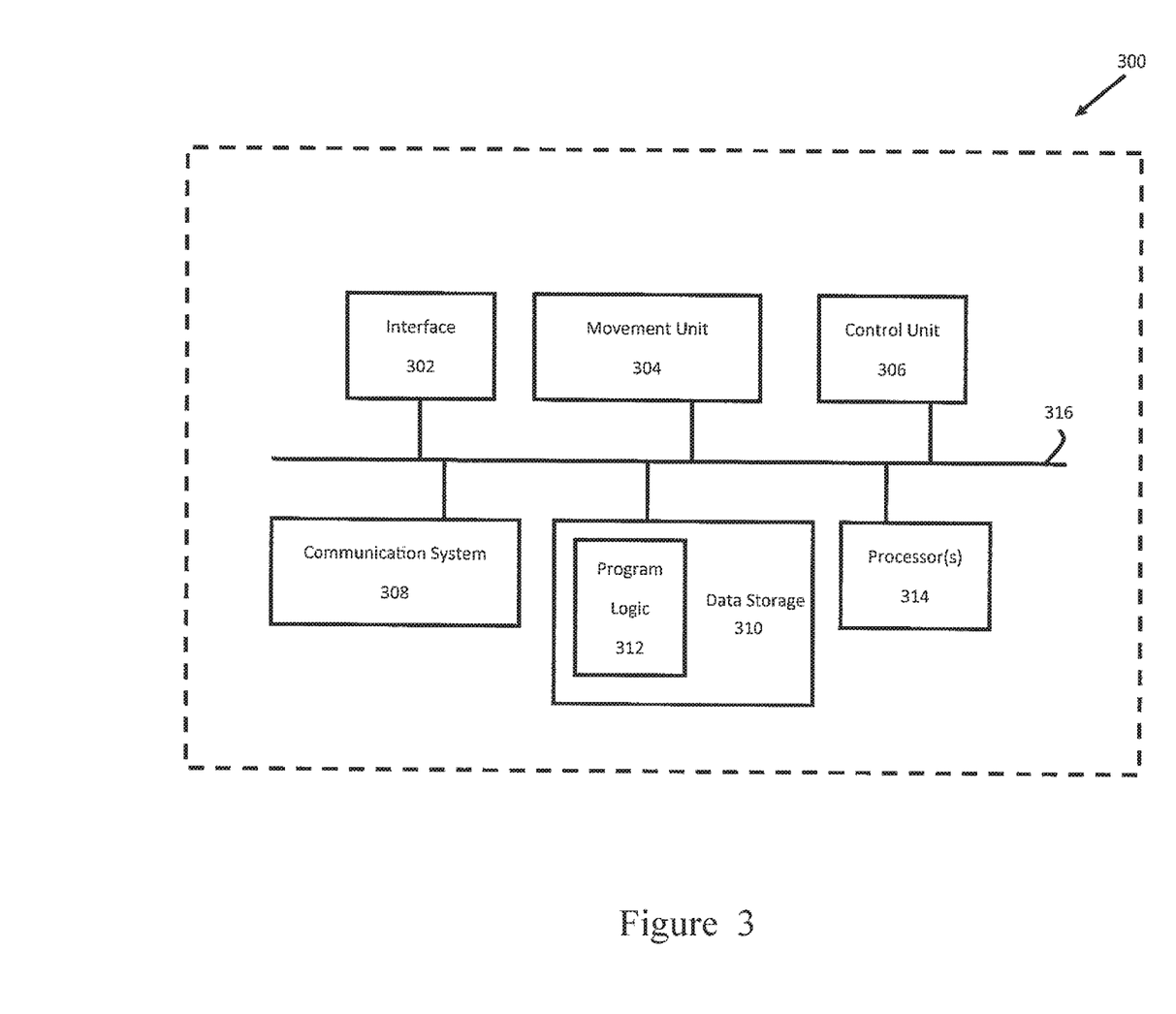
FIG. 3 illustrates an example block diagram of a computing device, according to an embodiment of the present disclosure.

FIG. 3 is a block diagram of a computing device 300, according to an example embodiment. In some examples, some components illustrated in FIG. 3 may be distributed across multiple computing devices (e.g., desktop computers, servers, hand-held devices, etc.). However, for the sake of the example, the components are shown and described as part of one example device. The computing device 300 may include an interface 302, a movement unit 304, a control unit 306, a communication system 308, a data storage 310, and a processor 314. Components illustrated in FIG. 3 may be linked together by a communication link 316. In some examples, the computing device 300 may include hardware to enable communication within the computing device 300 and another computing device (not shown). In one embodiment, the robotic device 140 or the robotic device 200 may include the computing device 300.

The interface 302 may be configured to allow the computing device 300 to communicate with another computing device (not shown). Thus, the interface 302 may be configured to receive input data from one or more devices. In some examples, the interface 302 may also maintain and manage records of data received and sent by the computing device 300. In other examples, records of data may be maintained and managed by other components of the computing device 300. The interface 302 may also include a receiver and transmitter to receive and send data. In some examples, the interface 302 may also include a user-interface, such as a keyboard, microphone, touch screen, etc., to receive inputs as well. Further, in some examples, the interface 302 may also interface with output devices such as a display, speaker, etc.

In one example, the interface 302 may receive an input indicative of location information corresponding to one or more elements of an environment in which a robotic device (e.g., robotic device 140, robotic device 200) resides. In this example, the environment may be an operating room in a hospital comprising a robotic device configured to function during a surgical procedure. The interface 302 may also be configured to receive information associated with the robotic device. For instance, the information associated with the robotic device may include operational characteristics of the robotic device and a range of motion with one or more components (e.g., joints 204, 208, 212, 216, 220, 224, and 230) of the robotic device (e.g., robotic device 140, robotic device 200).

The control unit 306 of the computing device 300 may be configured to run control software which exchanges data with components (e.g., robot arm 141, robot pedal 142, joints 204, 208, 212, 216, 220, 224, and 230, manipulator 228, etc.) of a robotic device (e.g., robotic device 140, robotic device 200) and one or more other devices (e.g., processing device 122, tracking device 130, etc.). The control software may communicate with a user through a user interface and display monitor (e.g., display 126) in communication with the robotic device. The control software may also communicate with the tracking device 130 and the processing device 122 through a wired communication interface (e.g., parallel port, USB, etc.) and/or a wireless communication interface (e.g., antenna, transceivers, etc.). The control software may communicate with one or more sensors to measure the efforts exerted by the user at the instrument T mounted to a robot arm (e.g., robot arm 141, link 226). The control software may communicate with the robot arm to control the position of the robot arm relative to the marker 150.

As described above, the control software may be in communication with the tracking device 130. In one scenario, the tracking device 130 may be configured to track the marker 150 that is attached to the patient P. By way of example, the marker 150 may be attached to a spinous process of a vertebra of the patient P. In this example, the marker 150 may include one or more infrared reflectors that are visible to the tracking device 130 to determine the location of the marker 150. In another example, multiple markers may be attached to one or more vertebrae and used to determine the location of the instrument T.

In one example, the tracking device 130 may provide updates in near real-time of the location information of the marker 150 to the control software of the robotic device 140. The robotic device 140 may be configured to receive updates to the location information of the marker 150 from the tracking device 130 via a wired and/or wireless interface. Based on the received updates to the location information of the marker 150, the robotic device 140 may be configured to determine one or more adjustments to a first position of the instrument T in order to maintain a desired position of the instrument T relative to the patient P.

In one embodiment, the control software may include independent modules. In an exemplary embodiment, these independent modules run simultaneously under a real time environment and use a shared memory to ensure management of the various tasks of the control software. The modules may have different priorities, such as a safety module having the highest priority, for example. The safety module may monitor the status of the robotic device 140. In one scenario, the safety module may send an instruction to the control unit 306 to stop the robot arm 141 when a critical situation is detected, such as an emergency stop, software failure, or collision with an obstacle, for example.

In one example, the interface 302 is configured to allow the robotic device 140 to communicate with other devices (e.g., processing device 122, tracking device 130). Thus, the interface 302 is configured to receive input data from one or more devices. In some examples, the interface 302 may also maintain and manage records of data received and sent by other devices. In other examples, the interface 302 may use a receiver and transmitter to receive and send data.

The interface 302 may be configured to manage the communication between a user and control software through a user interface and display screen (e.g., via displays 123 and 124). The display screen may display a graphical interface that guides the user through the different modes associated with the robotic device 140. The user interface may enable the user to control movement of the robot arm 141 associated with the beginning of a surgical procedure, activate a given mode to be used during a surgical procedure, and stop the robot arm 141 if needed, for example.

The movement unit 304 may be configured to determine the movement associated with one or more components of the robot arm 141 to perform a given procedure. In one embodiment, the movement unit 304 may be configured to determine the trajectory of the robot arm 141 using forward and inverse kinematics. In one scenario, the movement unit 304 may access one or more software libraries to determine the trajectory of the robot arm 141. In another example, the movement unit 304 is configured to receive one or more instructions for actuating the one or more components of the robotic device 140 from the processing device 122 according to a determined range of movement of a surgical tool at a surgical site.

The movement unit 304 may include a force module to monitor the forces and torques measured by one or more sensors coupled to the robot arm 141. In one scenario, the force module may be able to detect a collision with an obstacle and alert the safety module.

The control unit 306 may be configured to manage the functions associated with various components (e.g., robot arm 141, pedal 142, etc.) of the robotic device 140. For example, the control unit 306 may send one or more commands to maintain a desired position of the robot arm 141 relative to the marker 150. The control unit 306 may be configured to receive movement data from a movement unit 304.

In one scenario, the control unit 306 can instruct the robot arm 141 to function according to a cooperative mode. In the cooperative mode, a user is able to move the robot arm 141 manually by holding the tool T coupled to the robot arm 141 and moving the instrument T to a desired position. In one example, the robotic device 140 may include one or more force sensors coupled to an end effector of the robot arm 141. By way of example, when the user grabs the instrument T and begins to move it in a direction, the control unit 306 receives efforts measured by the force sensor and combines them with the position of the robot arm 141 to generate the movement desired by the user.

In one scenario, the control unit 306 can instruct the robot arm 141 to function according to a given mode that will cause the robotic device 140 to maintain a relative position of the instrument T to a given IR reflector or emitters (e.g., the marker 150). In one example, the robotic device 140 may receive updated position information of the marker 150 from the tracking device 130 and adjust as necessary. In this example, the movement unit 304 may determine, based on the received updated position information of the marker 150, which joint(s) of the robot arm 141 need to move in order to maintain the relative position of the instrument T with the marker 150.

In another scenario, a restrictive cooperative mode may be defined by a user to restrict movements of the robotic device 140. For the example, the control unit 306 may restrict movements of the robot arm 141 to a plane or an axis, according to user preference. In another example, the robotic device 140 may receive information pertaining to one or more predetermined boundaries within the surgical site that should not intersect with a surgical tool or implant based on a user guided movement of the robot arm 141.

In one embodiment, the robotic device 140 may be in communication with the processing device 122. In one example, the robotic device 140 may provide the position and orientation data of the instrument T to the processing device 122. In this example, the processing device 122 may be configured to store the position and orientation data of the instrument T for further processing. In one scenario, the image processing device 122 may use the received position and orientation data of the instrument T to overlay a virtual representation of the instrument T on display 126.

In one embodiment, a sensor configured to detect a pressure or force may be coupled to the last joint of the robot arm (e.g., link 226). Based on a given movement of the robot arm, the sensor may provide a reading of the pressure exerted on the last joint of the robot arm to a computing device (e.g., a control unit of the robotic device). In one example, the robotic device may be configured to communicate the force or pressure data to a computing device (e.g., processing device 122). In another embodiment, the sensor may be coupled to an instrument such as a retractor. In this embodiment, the force or pressure exerted on the retractor and detected by the sensor may be provided to the robotic device (e.g., robotic device 140, robotic device 200) or a computing device (e.g., processing device 122) or both for further analysis.

In one scenario, the robotic device may access movement data stored in a memory of the robotic device to retrace a movement along a determined motion path. In one example, the robotic device may be configured to move the surgical tool along the determined motion path to reach or move away from the surgical site.

In another scenario, once the instrument coupled to a robot arm (e.g., robot arm 141, links 206, 210, 214, 218, 222, and 226) of a robotic device reaches a desired pedicle screw trajectory, the robotic device may be configured to receive an input from the surgeon to travel along the desired pedicle screw trajectory. In one example, the surgeon may provide an input to the robotic device (e.g., depressing the pedal 142) to confirm the surgeon's decision to enable the robotic device to travel along the desired pedicle screw trajectory. In another example, a user may provide another form of input to either the robotic device or the computing device to assist with movement of an instrument along a determined motion path.

In one scenario, once the robotic device has received confirmation to travel along the desired pedicle screw trajectory, the robotic device may receive instructions from the movement unit 304 to pivot from the current trajectory to the desired pedicle screw trajectory. The movement unit 304 may provide the control unit 306 the required movement data to enable the robotic device to move along the desired pedicle screw trajectory.

In another aspect, a robotic device (e.g., robotic device 140, robotic device 200) may be configured to pivot about an area of significance based on the captured pose of a surgical tool (e.g., instrument T). For example, the robotic device may be configured to pivot a retractor about the tip of the retractor so that all the steps associated with retraction of soft tissue do not need to be repeated. In one example, the movement unit 304 may determine the trajectory required to pivot the retractor.

In one example, the robotic device may be coupled to a retractor that is holding soft tissue away from a surgical site. In this example, a surgeon may need to slightly reposition the retractor due to a patient movement. To do so, the surgeon may activate a mode on the robotic device that causes the retractor to pivot by moving the robot arm (e.g., robot arm 141, links 206, 210, 214, 218, 222, and 226) according to a trajectory determined by the movement unit 304. In one example, a user may input the direction and amount of movement desired via a computing device (e.g., the processing device 122, computing device 300). After the direction and amount of movement have been entered, the user (e.g., a surgeon) may interface with the robotic device (e.g., depress the pedal 142) to begin the movement of the instrument coupled to the robot arm. In one example, the robotic device may allow a user to view a different aspect of the anatomy without disengaging from a docking point.

In another example, the movement unit 304 may provide one or more trajectories for moving the surgical tool (e.g., instrument T) based on the captured pose of the surgical tool to a computing device (e.g., processing device 122) for display on display 126. In this example, a user may choose from one or more limited movements associated with a given step of a surgical procedure. For example, the one or more limited movements may be associated with a specific direction and amount of movement to be performed through the use of one or more buttons coupled to the robotic device 140 and by an individual applying a force to a portion of the robotic device 140.

In one scenario, the robot arm of the robotic device may be coupled to an instrument such as a dilator. In this scenario, the robotic device may receive one or more commands to pivot about the distal end of the dilator by a predetermined amount of degrees. The movement unit 304 may be configured to determine the trajectory necessary to perform the pivot and provide the determined trajectory information to the control unit 306 for moving the robotic device.

In another aspect, one or more infrared (IR) reflectors or emitters may be coupled to a robot arm (e.g., robot arm 141, links 206, 210, 214, 218, 222, and 226) of the robotic device (e.g., robotic device 140, robotic device 200). In one scenario, the tracking device 130 may be configured to determine the location of the one or more IR reflectors or emitters prior to beginning operation of the robotic device. In this scenario, the tracking device 130 may provide the location information of the one or more IR reflectors or emitters to a computing device (e.g., processing device 122, computing device 300) for further processing.

In one example, the processing device 122 or computing device 300 may be configured to compare the location information of the one or more IR reflectors or emitters coupled to the robot arm with data stored on a local or remote database that contains information about the robotic device (e.g., a geometric model of the robotic device) to assist in determining a location or position of the robot arm. In one example, the processing device 122 may determine a first position of the robot arm from information provided by the tracking device 130. In this example, the processing device 122 may provide the determined first position of the robot arm to the robotic device or a computing device (e.g., computing device 300). In one example, the robotic device may use the received first position data to perform a calibration of one or more elements (e.g., encoders, actuators) associated with the one or more joints of the robot arm.

In one scenario, an instrument coupled to the robot arm of the robotic device may be used to determine a difference between an expected tip location of the instrument and the actual tip location of the instrument. In this scenario, the robotic device may proceed to move the instrument to a known location by the tracking device 130 so that the tip of the tool is in contact with the known location. The tracking device 130 may capture the location information corresponding to the one or more IR reflectors or emitters coupled to the robot arm and provide that information to the robotic device or a computing device (e.g., processing device 122, computing device 300). Further, either the robotic device or the computing device may be configured to adjust a coordinate system offset between the robotic device and the tracking device 130 based on the an expected tip location of the tool and the actual tip location of the tool.

In another aspect, a force or pressure sensor may be coupled to a robot arm (e.g., robot arm 141, links 206, 210, 214, 218, 222, and 226) of a robotic device (e.g., robotic device 140, robotic device 200). In one example, the force or pressure sensor may be located on an end effector of the robot arm. In another example, the force or pressure sensor may be coupled to a given joint of the robotic arm. The force or pressure sensor may be configured to determine when a force or pressure reading is above a resting threshold. The resting threshold may be based on a force or pressure experienced at the sensor when the end effector is holding the instrument without any additional forces or pressure applied to the instrument (e.g., a user attempting to move the instrument). In one example, the robot arm may stop moving if the force or pressure reading is at or below the resting threshold.

In one example, the movement of the robot arm 141 may be controlled by depression of the pedal 142. For example, while the pedal 142 is depressed, the control unit 306 and the movement unit 304 may be configured to receive any measures of force or pressure from the one or more force sensors and used the received information to determine the trajectory of the robot arm 141.

In another example, the movement of the robot arm 141 may be regulated by how much the pedal 142 is depressed. For example, if the user depresses the pedal 142 to the full amount, the robot arm 141 may move with a higher speed compared to when the pedal 142 is depressed at half the amount. In another example, the movement of the robot arm 141 may be controlled by a user interface located on the robotic device.

In one example, the robotic device (e.g., robotic device 140, robotic device 200) may be configured to store, in a local or remote memory, movement data that corresponds to a determined range of movement associated with a surgical tool. In this example, the robotic device may be configured to only travel in one or more directions as defined by the determined range of movement.

In another example, the instrument coupled to the robot arm may include a switch that is in communication with the robotic device. The switch may be in the form of a button that provides a signal to the robotic device to move the robot arm according to the force detected by the force or pressure sensors associated with the end effector or one or more joints of the robot arm. In this example, when the surgeon lets go of the switch, the robotic device will interpret that action as a stopping command and maintain the position of the instrument.

In one example, the surgeon may incorporate the use of a three-dimensional image of the spine and define one or more planes that the instrument should not traverse. In this example, despite force or pressure sensor detecting a force to move the instrument, the robot arm will not allow the surgeon to move the instrument past the defined one or more planes according to the constraints associated with the predefined plan. By way of example, the robotic device may be configured to provide an alert to the surgeon as the instrument approaches the one or more restricted planes.

In another aspect, a robotic device (e.g., robotic device 140, robotic device 200) may be used to navigate one or more surgical instruments and provide the navigation information to a computing device (e.g., processing device 122, computing device 300) for further processing. In one example, the computing device may be configured to determine a virtual representation of the surgical instrument. Further, the computing device may be configured to overlay the virtual representation of the surgical instrument on a two-dimensional or three-dimensional image of the surgical site.

In one example, the robotic device may perform a calibration procedure between the tracking device 130 in order to remove the dependence on the tracking device 130 for location information in the event that a line of sight between the robotic device and the tracking device 130 is blocked. In one example, using a robotic device which has been registered to a navigation system, as described herein, and a patient's three-dimensional image that corresponds to the surgical site may allow the robotic device to become independent of the degradation of accuracy with distance associated with the tracking device 130.

The communication system 308 may include a wired communication interface (e.g., parallel port, USB, etc.) and/or a wireless communication interface (e.g., antenna, transceivers, etc.) to receive and/or provide signals from/to external devices. In some examples, the communication system 308 may receive instructions for operation of the processing device 122. Additionally or alternatively, in some examples, the communication system 308 may provide output data.

The data storage 310 may store program logic 312 that can be accessed and executed by the processor(s) 314. The program logic 312 may contain instructions that provide control to one or more components of the processing device 122, the robotic device 140, the robotic device 200, etc. For example, program logic 312 may provide instructions that adjust the operation of the robotic device 200 based one on or more user defined trajectories associated with a portable instrument. The data storage 310 may comprise one or more volatile and/or one or more non-volatile storage components, such as optical, magnetic, and/or organic storage, and the data storage may be integrated in whole or in part with the processor(s) 314.

The processor(s) 314 may comprise one or more general-purpose processors and/or one or more special-purpose processors. To the extent the processor 314 includes more than one processor, such processors may work separately or in combination. For example, a first processor may be configured to operate the movement unit 304, and a second processor of the processors 314 may operate the control unit 306.

Still further, while each of the components are shown to be integrated in the processing device 122, robotic device 140, or robotic device 200, in some embodiments, one or more components may be removably mounted to otherwise connected (e.g., mechanically or electrically) to the processing device 122, robotic device 140, or robotic device 200 using wired or wireless connections.

In another example, the robotic device may assist with tracking instruments coupled to the robot arm in one or more locations during a surgical procedure. Tracking the instruments via the movement of the robotic device may enable the instrument to be placed in a location that is difficult for a surgeon to see. For example, the instrument may be placed behind a drape but tracked via the robotic device and a computing device (e.g., processing device 122, computing device 300). In another example, the robotic device may assist with tracking the movements of the patient under a sterile barrier. In this example, the robotic device may be used to reposition a bed to keep the patient in a known orientation during a surgical procedure.

In another aspect, a robotic device (e.g., robotic device 140, robotic device 200) may be configured to receive one or more constraints corresponding to the movement associated with a robot arm (e.g., robot arm 141, links 206, 210, 214, 218, 222, and 226). For example, a surgeon may want to define an area that the robotic device is permitted to move around in during a surgical procedure. In one scenario, the surgeon may view a three-dimensional representation of the patient's anatomy on the display 126 and input one or more boundaries associated with movement of the robot arm. In another scenario, the surgeon may view a two-dimensional representation of the patient's anatomy on the display and define the one or more boundaries through a touch screen associated with display 126.

In one example, the surgeon may input the path of the surgical procedure prior to beginning the surgical procedure. For example, the surgeon may use a two-dimensional or three-dimensional image of the patient's anatomy and determine a path for reaching a surgical site. In one example, a computing device (e.g., processing device 122, computing device 300) may store information corresponding to the predetermined path and provide the information to the robotic device prior to the beginning of the surgical procedure. Once the robotic device is aware of the position of the robotic device relative to the patient, the movement unit 304 may use the information corresponding to the predetermined path to determine one or more trajectories allowed.

In another example, the path for reaching a surgical site may include constraints corresponding to a specific depth of penetration during a single pass of the robot arm. For example, the movement of the robot arm may be limited by a maximum amount chosen by the surgeon. In one scenario, the limit may be informed by another sensor associated with detecting an electromyography (EMG) response.

In one scenario, the robot arm may be coupled to an instrument that is used to remove bone. In this scenario, the robotic device may receive one or more commands associated with removing a certain amount of the bone, for example one millimeter of bone removal. The robotic device may be configured to provide the surgeon a notification when the bone removal procedure is complete via an audible or visual signal. In another scenario, the robotic device may receive one or more commands associated with continuing to remove bone until 2 millimeters of the bone remains.

In another example, a path limiting the movement of robot arm may correspond to one or more inputs corresponding to anatomical segmentation. For example, a surgeon may select a particular vertebra to limit the movements of the robot arm to that particular vertebra. By way of example, the robotic device may be further instructed to limit the movement of the robot arm to a specific portion of a vertebra (e.g., the spinous process, etc.).

In another aspect, a robotic device (e.g., robotic device 140, robotic device 200) may be coupled to an end effector that assists in retraction of soft tissue and insertion of a fastener to a vertebra of a patient. By way of example, the plates used in spine surgery have known geometries that a fastener will be able to correctly engage with and lock into its final position. The plates typically require screw/drill guides to control placement of the threaded fasteners. The guides often stick out and are impeding soft tissues that cannot support long durations of retraction.

In one embodiment, an end effector may be coupled to a robot arm (e.g., robot arm 141, links 206, 210, 214, 218, 222, and 226) and assist with placement of a fastener. In one scenario, the robotic device may receive three-dimensional geometric information about a plate being used in a surgical procedure from a computing device (e.g., processing device 122, computing device 300).

In one example, a given plate may require four fasteners to be installed during a surgical procedure. In this example, the robotic device may use the end effector to retract the soft tissue that corresponds to a first fastener position of the given plate based on a trajectory determined by the movement unit 304. Further, the movement unit 304 may also be configured to determine an optimal trajectory for placement of the fastener through the given plate. Following the placement of the first fastener, the robotic device may be configured to move the end effector in a manner that allows for the soft tissue to return to its original position and move to retract the soft tissue that corresponds to a second fastener position of the given plate. In this example, the robotic device may minimize the time that the soft tissue is retracted and thereby decrease a risk to damaging the soft tissue while installing each of the fasteners to the given plate.

In one example, the movement unit 304 may be configured to determine the amount of angulation that is associated with a given plate to provide additional ease for placement of a fastener. By way of example, a surgeon may guide the robot arm (e.g., robot arm 141, links 206, 210, 214, 218, 222, and 226) until the robotic device detects intersection of a predetermined optimal path as described above. In this example, the robotic device may be configured to pivot at the intersection predetermined optimal path and continue along the path to install the fastener on the given plate. In one example, the end effector used to install the fasteners may incorporate additional sensors used to detect any issues that may occur during the surgical procedure while retracting the soft tissue.

In another aspect, a robotic device (e.g., robotic device 140, robotic device 200) may use location information captured by the tracking device 130 to determine the position of an instrument coupled to a robot arm (e.g., robot arm 141, links 206, 210, 214, 218, 222, and 226) relative to the patient. In one embodiment, the robotic device may use movement information determined by encoders associated with one or more joints (e.g., joints 204, 208, 212, 216, 220, and 224) of the robotic device to determine the position of the surgical tool after a calibration procedure between the robotic device and the tracking device 130. In another embodiment, the tracking device 130 may provide location information to a computing device (e.g., processing device 122, computing device 300) to assist with tracking the robotic device during the surgical procedure.

In one example, the tracking device 130 may track the position of the instrument coupled to the robot arm based on one or more IR reflectors or emitters. For example, the tracking device 130 may detect the IR reflectors or emitters coupled to the tool and provide location information to the processing device 122. The processing device 122 may be configured to compare the last known position information of the IR reflectors or emitters coupled to the instrument with the most recent position information and determine a change in position associated with the instrument.

In one embodiment, based on the determined change in position of the instrument, the processing device 122 may be configured to determine the image data associated with one or more changes in volume of a disc or bone that corresponds to the position of the instrument. In one example, based on the determined image data, the amount of disc or bone removed could be represented virtually via display 126. For example, the amount of disc or bone could be shown by deleting data corresponding to the paths that the instrument has reached based on the position information of the IR reflectors or emitters coupled to the instrument. In another example, in a procedure that includes the use of a drill on a bone in one or more passes, each pass is expected to remove a part of the patient's anatomy. In this example, with each pass of the surgical tool over the disc, the image data (e.g., pixels) representing the amount of removed disc may be changed to a different color (e.g., red) to denote a corresponding volume of the disc has been removed.

In another example, a virtual representation of the path associated with the instrument coupled to the robot arm may be overlaid on the corresponding locations of the patient's anatomy. The virtual representation of the path may be displayed with a variety of visual effects to denote multiple passes by the instrument over a particular area of the spine. Further, as described above, the robotic device may be configured to prevent a user from continuing to remove disc space based on one or more predetermined boundaries corresponding to the movement of the surgical tool.

In another aspect, the robotic device (e.g., robotic device 140, robotic device 200) may include more than one robot arm (e.g., robot arm 141, links 206, 210, 214, 218, 222, and 226). In one scenario, as described above, the robotic device and the tracking device 130 may have completed a registration process to correct any offset between each of their coordinate systems. In this scenario, in addition to completion of the registration process, the processing device 122 may be configured to receive a 3D scan of the spine of the patient. In one embodiment, the robotic device may be configured to maintain a spinal alignment of the patient according to a preoperative plan for spinal alignment.

In one example, the robotic device may use an end effector that is configured for gripping a critical element of the surgical procedure. For example, the robotic device may use a first gripper coupled to the robot arm to grip a first pedicle screw and a second gripper coupled to a second robot arm to grip a second pedicle screw. The robotic device may be configured to provide a computing device (e.g., processing device 122, computing device 300) the position information associated with each of the first and second robot arms. Based on the received position information, the computing device may determine a current spinal alignment. Further, the computing device may analyze the current spinal alignment to determine a required correction of the spine during a surgical procedure.

For example, analysis of the current spinal alignment may include comparing the current spinal alignment with the preoperative plan for spinal alignment. In one scenario, the processing computing device may determine an offset between the current spinal alignment and the preoperative plan for spinal alignment. Further, the computing device may be configured to determine an amount of movement needed to bring the current spinal alignment to the preoperative plan for spinal alignment.

In one scenario, the computing device may determine that a rotation of two degrees by the first robot arm will help restore the current spinal alignment to the preoperative plan. In this scenario, the computing device may provide the rotation information needed to robotic device. By way of example, the movement unit 304 may determine the necessary trajectory to achieve the rotation of two degrees by the robot arm. Based on the determined trajectory, the control unit 306 may provide the one or more commands to actuate the one or more joints of the robot arm.

In another scenario, the processing device 122 may determine that a rotation of two degrees by a first robot arm and a rotation of one degree by a second robot arm will restore the current spinal alignment to the preoperative plan. In this scenario, the processing device 122 may provide the necessary rotation needed to the robotic device 140. As described above, the calculations module of the robotic device 140 may determine the necessary trajectory to achieve the required movements by the first and second robot arms.

In another scenario, the robotic device may be supporting the operating table that the patient has been placed on. In this scenario, the robotic device may also be configured to adjust the operating table in addition to performing one or more movements of the spine to achieve spinal alignment.

In another aspect, the robot arm (e.g., robot arm 141, links 206, 210, 214, 218, 222, and 226) of the robotic device (e.g., robotic device 140, robotic device 200) may be configured to receive an ultrasonic probe. In one scenario, the ultrasonic probe is held by the robot arm in a known orientation so that it registers the location of the anatomy in the image for subsequent instrumentation relative to the image with either the robot arm or a co-registered navigation system (e.g., registration between robotic device 140 or robotic device 200 and tracking device 130).

In one example, one or more IR emitters or reflectors may be coupled to the ultrasonic probe. The tracking device 130 may capture the location information of the one or more IR emitters or reflectors coupled to the ultrasonic probe. In this example, the location of the robot arm 141 may be tracked via the use of the one or more IR emitters or reflectors and co-register the robot arm and the ultrasonic probe with the images that are captured by the ultrasonic probe.

In another aspect, a robot arm (e.g., robot arm 141, links 206, 210, 214, 218, 222, and 226) of the robotic device (e.g., robotic device 140, robotic device 200) may be coupled to a pressure-sensing endplate pusher. The pressure-sensing endplate pusher may include two plates that may be actuated separately. In one scenario, a first plate of the pressure-sensing endplate pusher may be applied to the lower endplate of an upper vertebra. In this scenario, a second plate of the pressure-sensing endplate pusher may be applied to the upper endplate of a lower vertebra. In one embodiment, the pressure-sensing endplate pusher may include one or more sensors for detecting a force on each of the first and second plates.

In one embodiment, the plates of the pressure-sensing endplate pusher are coupled to an actuator that enables movement of each plate separately. In one scenario, the robotic device can provide the feedback force (pressure since the area of plate is known) to a computing device (e.g., processing device 122) for further analysis. Each of the plates will be of significant size so that they cover the same area as an implant to be used when fully inserted between two vertebrae. This will enable a realistic biomechanical force on the anatomy and can provide feedback to ensure that the patient is not loaded to a level that causes a subsequent decompression between the two vertebrae.

The plates will act on each endplate to provide the appropriate height and angle to allow the surgeon to properly size the implant height and angle to maximize indirect decompression and minimize stress on the endplates that would cause subsidence. In one scenario, the robotic device may be provided with patient demographic information in addition to bone density to determine a level of force that is applied through the use of the pressure-sensing endplate pusher.

In another aspect, a robot arm (e.g., robot arm 141, links 206, 210, 214, 218, 222, and 226) of the robotic device (e.g., robotic device 140, robotic device 200) may be coupled to a retractor. In one embodiment, the retractor may include one or more sensors for detecting the pressure exerted on the retractor. Since the retractor is controlled by the robotic device, the robotic device may be configured to provide the pressure information to a computing device (e.g., processing device 122, processing device 300).

In one example the computing device may analyze the pressure data to determine if one or more soft tissues are associated with a pressure that exceeds a safety threshold. In this example, the computing device may communicate this information to a user via display 126 as well as instruct the robotic device to reduce the amount of retraction associated with the soft tissues.

Since the force on the robot is known, and so is the retractor area, the computing device may be configured to convert both of those into a pressure. In one example, display 126 may be configured to display a graphical user interface (GUI) that can provide a graduated indicator of how much pressure is applied relative to a maximum amount of pressure allowed. In one embodiment, the robotic device may be configured to hold the load at any spot along that relative gauge. In another example, according to a preoperative plan, the robotic device may be configured to only retract to a certain pressure.

Figure 4:
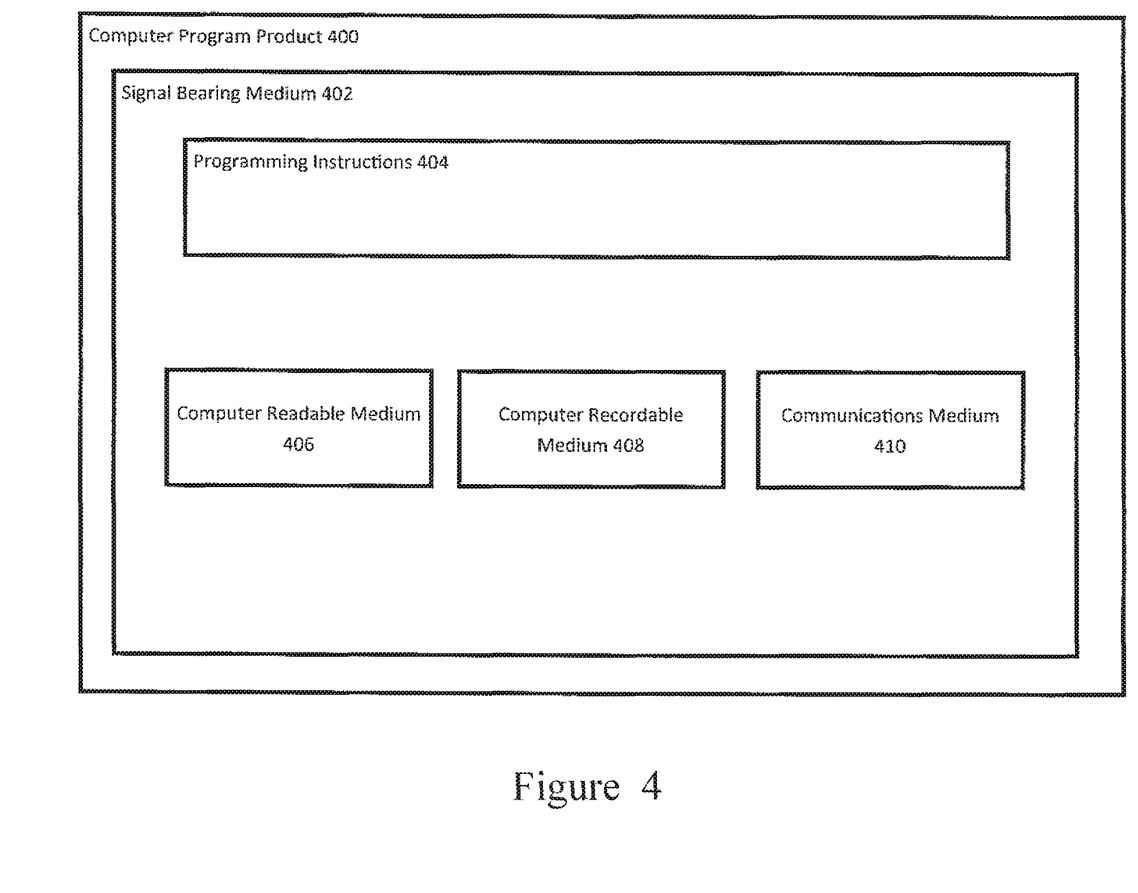
FIG. 4 illustrates an example computer medium, according to an embodiment of the present disclosure.

FIG. 4 depicts an example computer readable medium configured according to an example embodiment. In example embodiments, an example system may include one or more processors, one or more forms of memory, one or more input devices/interfaces, one or more output devices/interfaces, and machine readable instructions that when executed by the one or more processors cause the system to carry out the various functions tasks, capabilities, etc., described above.

As noted above, in some embodiments, the disclosed techniques (e.g., functions of the robotic device 140, robotic device 200, processing device 122, computing device 300, etc.) may be implemented by computer program instructions encoded on a computer readable storage media in a machine-readable format, or on other media or articles of manufacture. FIG. 4 is a schematic illustrating a conceptual partial view of an example computer program product that includes a computer program for executing a computer process on a computing device, arranged according to at least some embodiments disclosed herein.

In one embodiment, an example computer program product 400 is provided using a signal bearing medium 402. The signal bearing medium 402 may include one or more programming instructions 404 that, when executed by one or more processors, may provide functionality or portions of the functionality described above with respect to FIGS. 1-3. In some examples, the signal bearing medium 402 may be a computer-readable medium 406, such as, but not limited to, a hard disk drive, a Compact Disc (CD), a Digital Video Disk (DVD), a digital tape, memory, etc. In some implementations, the signal bearing medium 402 may be a computer recordable medium 408, such as, but not limited to, memory, read/write (R/W) CDs, R/W DVDs, etc. In some implementations, the signal bearing medium 402 may be a communication medium 410 (e.g., a fiber optic cable, a waveguide, a wired communications link, etc.). Thus, for example, the signal bearing medium 402 may be conveyed by a wireless form of the communications medium 410.

The one or more programming instructions 404 may be, for example, computer executable and/or logic implemented instructions. In some examples, a computing device may be configured to provide various operations, functions, or actions in response to the programming instructions 404 conveyed to the computing device by one or more of the computer readable medium 406, the computer recordable medium 408, and/or the communications medium 410.

The computer readable medium 406 may also be distributed among multiple data storage elements, which could be remotely located from each other. The computing device that executes some or all of the stored instructions could be an external computer, or a mobile computing platform, such as a smartphone, tablet device, personal computer, wearable device, etc. Alternatively, the computing device that executes some or all of the stored instructions could be remotely located computer system, such as a server.

Figure 5:
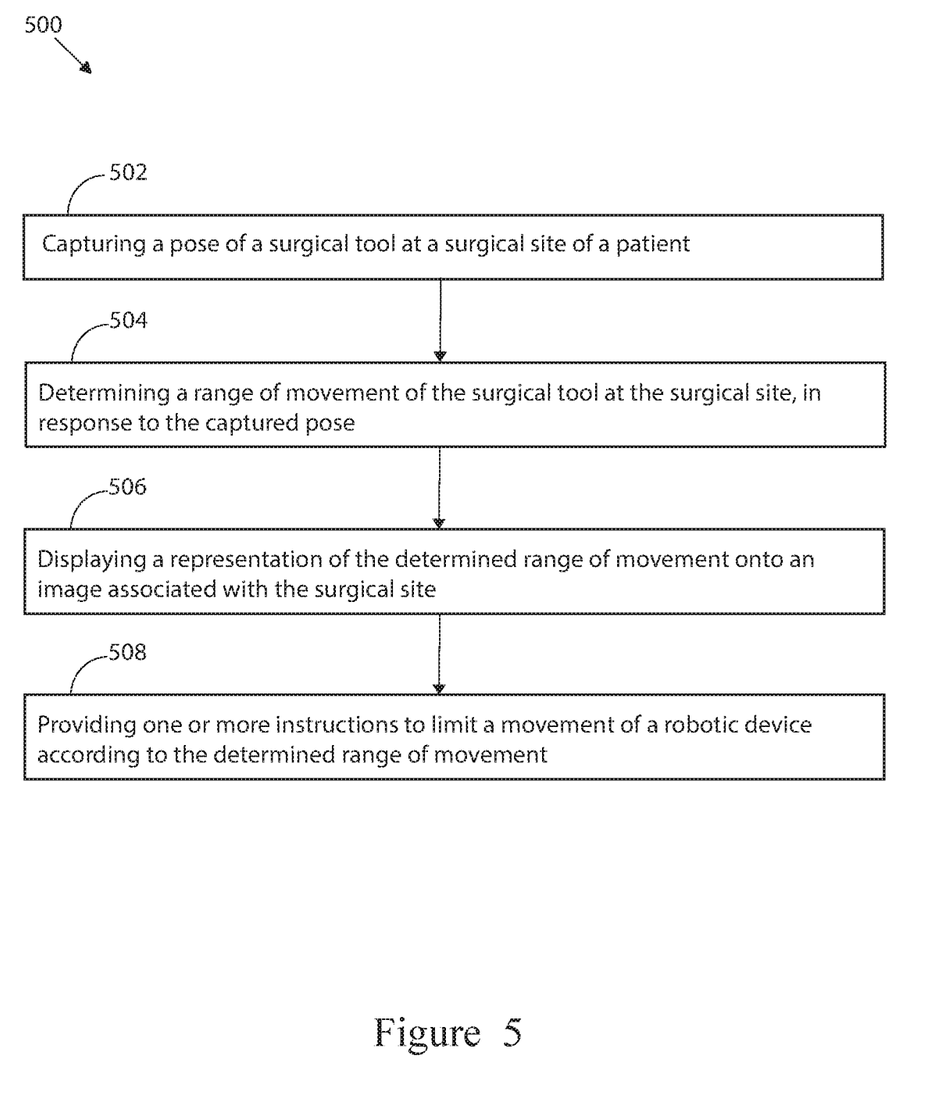
FIG. 5 illustrates a flow diagram of an example method during a surgical procedure, according to an embodiment of the present disclosure.
Figure 6:
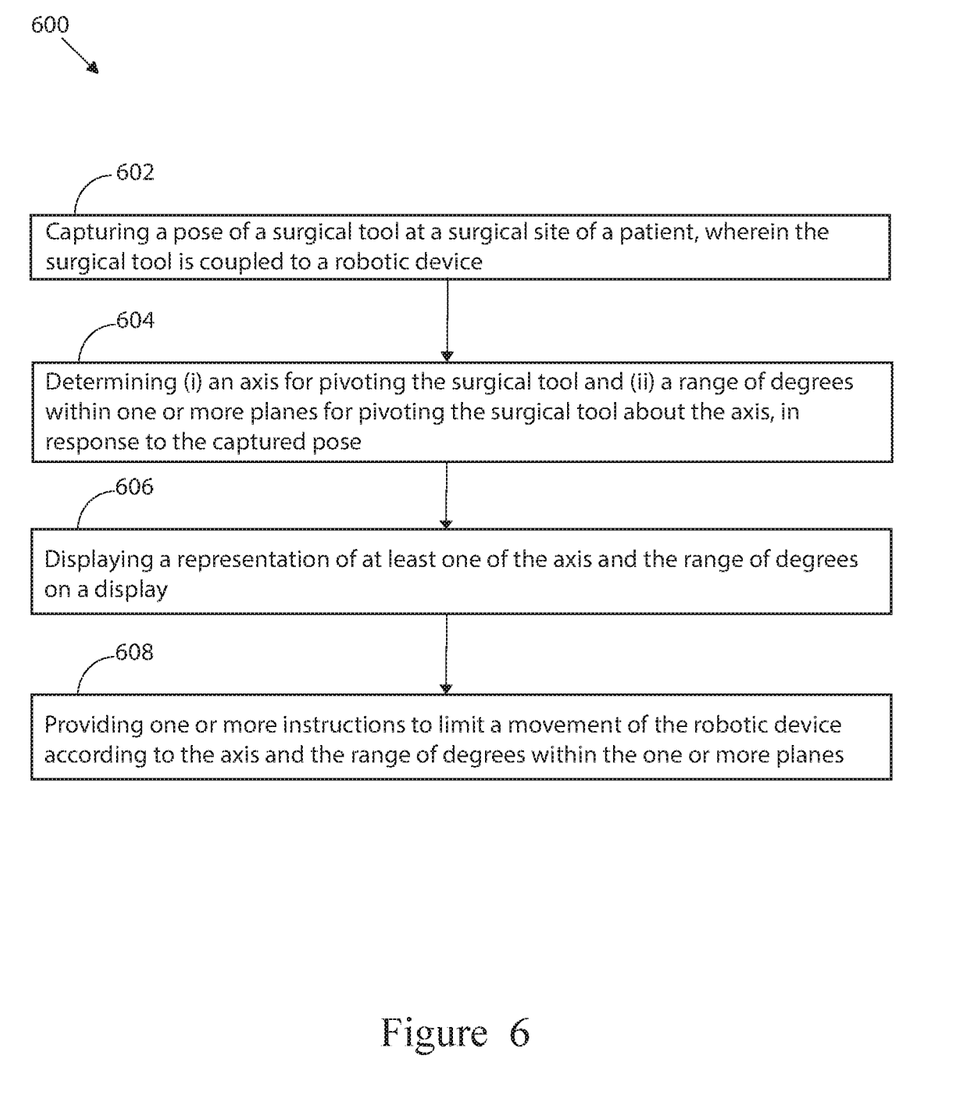
FIG. 6 illustrates another flow diagram of an example method during a surgical procedure, according to an embodiment of the present disclosure.

FIGS. 5 and 6 are flow diagrams of example methods during a surgical procedure, in accordance with at least one or more embodiments described herein. Although the blocks in each figure are illustrated in a sequential order, the blocks may in some instances be performed in parallel, and/or in a different order than those described therein. Also, the various blocks may be combined into fewer blocks, divided into additional blocks, and/or removed based upon the desired implementation.

In addition, the flow diagrams of FIGS. 5 and 6 show the functionality and operation of possible implementations of the present embodiment. In this regard, each block may represent a module, a segment, or a portion of program code, which includes one or more instructions executable by a processor for implementing specific logical functions or steps in the process. The program code may be stored on any type of computer readable medium, for example, such as a storage device including a disk or hard drive. The computer readable medium may include non-transitory computer-readable media that stores data for short periods of time, such as register memory, processor cache, or Random Access Memory (RAM), and/or persistent long term storage, such as read only memory (ROM), optical or magnetic disks, or compact-disc read only memory (CD-ROM), for example. The computer readable media may be able, or include, any other volatile or non-volatile storage systems. The computer readable medium may be considered a computer readable storage medium, a tangible storage device, or other article of manufacture, for example.

Alternatively, each block in FIGS. 5 and 6 may represent circuitry that is wired to perform the specific logical functions in the process. Illustrative methods, such as those shown in FIGS. 5 and 6, may be carried out in whole in or in part by a component or components in the cloud and/or system 100 of FIG. 1. However, it should be understood that the example methods may instead be carried out by other entities or combinations of entities (i.e., by other computing devices and/or combination of computer devices), without departing from the scope of the invention. For example, functions of the methods of FIGS. 5 and 6 may be fully performed by a computing device (or components of a computing device such as one or more processors), or may be distributed across multiple components of the computing device, across multiple computing devices (e.g., control unit 118 and image processing device 122 of FIG. 1), and/or across a server.

Referring to FIG. 5, an example method 500 during a surgical procedure may include one or more operations, functions, or actions as illustrated by blocks 502-508. In one embodiment, the method 500 is implemented in whole or in part by the system 100 of FIG. 1.

As shown by block 502, the method 500 includes capturing a pose of a surgical tool at a surgical site of a patient. In one example, the tracking device 130 may be configured to capture one or more images of the instrument T as the instrument T is used in a surgical procedure. The captured one or more images are processed so as to determine orientation and position data associated with one or more IR markers coupled to the instrument T. The determined orientation and position data associated with the one or more IR markers is then used to determine the three-dimensional pose data of the instrument T over a given period of time. In one example, the instrument T may be placed at a known location within the operating room to indicate the trigger of capturing motion data. Continuing with this example, the processing device 122 may be configured to determine when the instrument T has not moved within a predetermined amount of time as an indicator to end the capture of motion data. In another example, a button may be depressed on a user interface, such as on the display device 126 or interface 125 to toggle between starting and stopping the capture of motion data associated with instrument T.

As shown by block 504, the method 500 includes in response to the captured pose, determining a range of movement of the surgical tool at the surgical site. In one example, the determined range of movement is based on a pivot of the surgical tool within an area of significance at the surgical site. In one example, the area of significance is based on a diameter of five millimeters.

In one example, the method 500 also includes determining a second range of movement corresponding to the captured pose. In this example, the method may also compare the range of movement to the second range of movement. Based on the comparison, the method may also include providing instructions to adjust a position of the surgical tool. For example, the processing device 122 may be configured to determine the second range of movement based on an offset of the current position of the surgical tool. In this example, the second range of movement may allow for additional degrees of rotation of the surgical tool by adjusting the current position of the surgical tool to the offset position.

In another example, the surgical site comprises a vertebra. In this example, the method may include determining the range of movement based on detection of one or more edges corresponding to the vertebra. For example, the processing device 122 may include computer executable instructions that are configured to perform a segmentation step. As used herein, "segmentation" describes a process that identifies individual vertebrae within three-dimensional image data so that the vertebrae can be separated and treated, manipulated, and displayed distinct from one another. The segmentation step may employ a segmentation algorithm that uses imaging processing and image recognition software to automate the spinal level segmentation process. In one embodiment, the computer executable instructions automatically identify and extract the spine curve, detect and identify each individual vertebra, until they are segmented from one another. One or more adaptive meshes may be applied to generate a segmented three-dimensional model of the spine. Each vertebra or other anatomical features can be separately colored to visibly enhance the bone-soft tissue interface, or just the margin can be colored.

Figure 7:
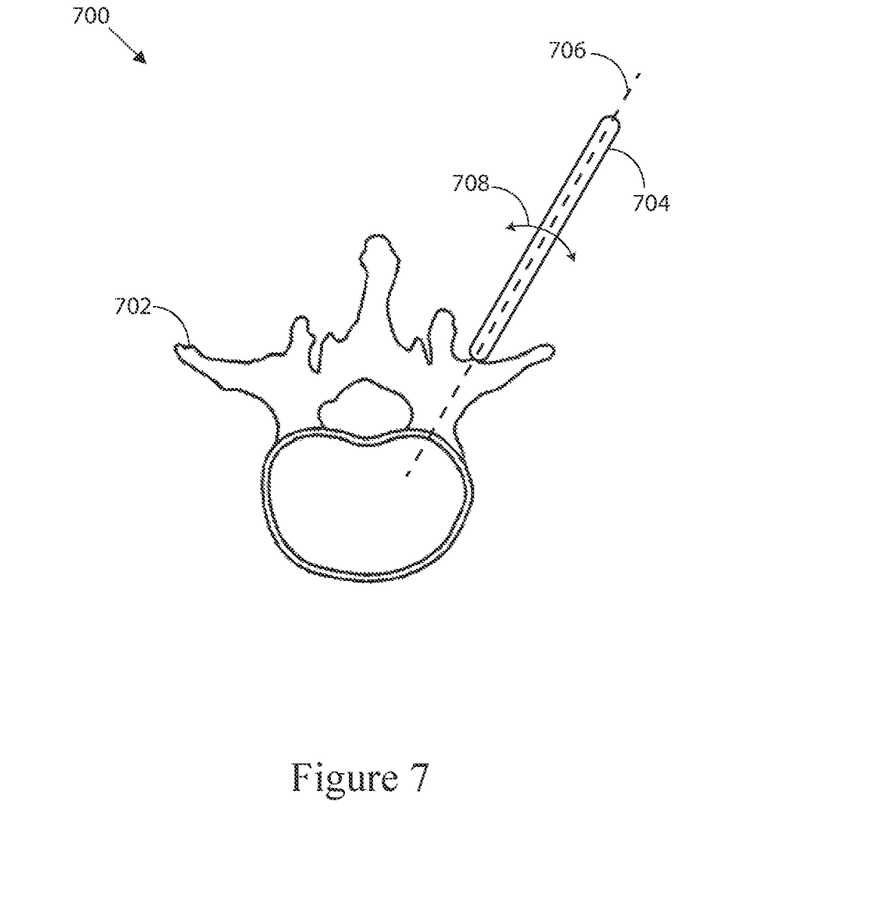
FIG. 7 illustrates an example image that may be displayed during a surgical procedure, according to an embodiment of the present disclosure.

As shown by block 506, the method 500 includes displaying a representation of the determined range of movement onto an image associated with the surgical site. Referring to FIG. 7, FIG. 7 illustrates an example two-dimensional image 700 of a surgical site that includes vertebra 702 and a surgical tool 704. In one example, the pose of the surgical tool 704 is captured and used to determine a range of movement of the surgical tool 704. In one example, a processing device (e.g., processing device 122) may be configured to determine an axis 706 for pivoting the surgical tool 704. The processing device may also be configured for determining a range of degrees 708 within one or more planes for pivoting the surgical tool 704 about the axis 706. In one example, the image 700 may be displayed on a display (e.g., display 126). This would enable a user (e.g., a surgeon) to view a representation of at least one of the axis 706 and the range of degrees 708 in order to make an informed decision before proceeding with a next step in the surgical procedure.

Referring back to FIG. 5, as shown by block 508, the method 500 includes providing one or more instructions to limit a movement of a robotic device according to the determined range of movement. In one example, the one or more instructions include robotic movements that limit an end effector of the robotic device to particular positions in space based on the determined range of movement. In one example, the method also includes providing instructions to stop any movement associated with the robotic device. In one example, the one or more instructions may be provided via a wireless or wired communication interface between the processing device 122 and the robotic device 140.

Referring to FIG. 6, an example method 600 during a surgical procedure may include one or more operations, functions, or actions as illustrated by blocks 602-608. In one embodiment, the method 600 is implemented in whole or in part by the system 100 of FIG. 1.

As shown by block 602, the method 600 includes capturing a pose of a surgical tool at a surgical site of a patient, wherein the surgical tool is coupled to a robotic device. Block 602 may be similar in functionality to block 502 of method 500.

As shown by block 604, the method 600 includes in response to the captured pose, determining (i) an axis for pivoting the surgical tool and (ii) a range of degrees within one or more planes for pivoting the surgical tool about the axis. Block 604 may be similar in functionality to block 504 of method 500.

As shown by block 606, the method 600 includes displaying a representation of at least one of the axis and the range of degrees on a display. Block 606 may be similar in functionality to block 506 of method 500. In one example, in order to form a pilot hole for pedicle screw placement in a vertebral pedicle with the aid of the robotic device 140, the instrument T is advanced by a surgeon to the pedicle target site where the pilot hole is to be formed. In this example, the tracking device 130 is configured to capture the position and orientation of instrument T and provide the position and orientation information to the processing device 122. Continuing with this example, the processing device 122 is configured to provide an image of the surgical site for display and a representation of at least one of the axis and the range of degrees on a display.

As shown by block 608, the method 600 also includes providing one or more instructions to limit a movement of the robotic device according to the axis and the range of degrees within the one or more planes. Block 608 may be similar in functionality to block 508 of method 500. In one example, a sequence of robot joint parameters, including joint angles, velocities, and/or accelerations may be determined for limiting the movement of the robotic device according to the axis and the range of degrees within the one or more planes. In one embodiment, robot movements may be modified in order to smooth motion curves of the robot and/or of the robot tool in order to avoid jerking or disconnected movements while a user is pivoting the surgical tool.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

What is claimed is:

1. A system comprising:
a surgical tool;
a tracking device;
an interface;
a robotic device having a robot arm with a manipulator that holds the surgical tool, wherein the surgical tool is at least partially manually movable by a user relative to the manipulator while the surgical tool is being held by the manipulator; and
a processing device comprising:
one or more processors; and
a non-transitory computer readable medium having stored thereon instructions that, when executed by the one or more processors, cause the one or more processors configured to:
capture, via the tracking device, a pose of a surgical tool at a surgical site of a patient;
determine, by the one or more processors, a range of movement of the surgical tool at the surgical site relative to the manipulator holding the surgical tool, based on the captured pose;
display, at the interface, a representation of the determined range of movement of the surgical tool onto an image associated with the surgical site; and
provide one or more instructions to limit a movement of the robotic device according to the determined range of movement of the surgical tool.

2. The system of claim 1, wherein the non-transitory computer readable medium having stored thereon instructions that, when executed by the one or more processors, further cause the system configured to:
determine a second range of movement corresponding to the captured pose;
compare the range of movement to the second range of movement; and
provide instructions to adjust a position of the surgical tool, based on the comparison.

3. The system of claim 1, wherein the surgical site comprises a vertebra, wherein determining the range of movement includes detection of one or more edges corresponding to the vertebra.

4. The system of claim 1, wherein providing instructions to limit a movement of a robotic device according to the determined range of movement comprises an instruction to stop any movement associated with the robotic device.

5. The system of claim 4, wherein the pivot of the surgical tool is based on a pivot about a distal end of the surgical tool.

6. The system of claim 1, wherein the non-transitory computer readable medium having stored thereon instructions that, when executed by the one or more processors, further cause the system configured to determine the range of movement of the surgical tool at the surgical site based on a selection of a particular vertebra.

7. The system of claim 1, wherein providing instructions to limit a movement of a robotic device according to the determined range of movement comprises an instruction to limit movement associated with the robotic device to at least one plane.

8. The system of claim 1, wherein the surgical tool is a retractor.

9. The system of claim 8, wherein the range of movement of the surgical tool is based on one or more arms of the retractor.

10. The system of claim 1, wherein to determine, by the one or more processors, a range of movement of the surgical tool at the surgical site relative to the robot arm, includes:
limiting the range of movement based on an electromyography response.

11. The system of claim 1, wherein the surgical tool is a dilator.

12. The system of claim 1, wherein the determined range of movement is based on a pivot of the surgical tool within a predetermined area of significance at the surgical site.

13. The system of claim 1,
wherein the surgical tool has one or more infrared reflectors or emitters coupled thereto; and
wherein the tracking device is configured to detect the infrared reflectors or emitters coupled to the surgical tool and provide location information to the processing device.

14. The system of claim 1,
wherein the instructions cause the one or more processors to: determine (i) an axis for pivoting the surgical tool and (ii) a range of degrees within one or more planes for pivoting the surgical tool about the axis based on the captured pose; and
wherein to display the representation includes to display a representation of one or both of the axis and the range of degrees.

15. The method of claim 14, wherein the surgical site comprises a vertebra, wherein determining the range degrees within the one or more plane includes detection of one or more edges corresponding to the vertebra.

16. The method of claim 1, wherein providing instructions to limit a movement of a robotic device according to the determined range of movement comprises an instruction to limit movement associated with the robotic device to at least one plane.

* * * * *